(12) United States Patent
Onuma

(10) Patent No.: US 9,551,723 B2
(45) Date of Patent: Jan. 24, 2017

(54) LIQUID REAGENT OF THYROID HORMONE-IMMOBILIZED CARRIER AND USE THEREOF

(75) Inventor: Naotsugu Onuma, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 698 days.

(21) Appl. No.: 13/365,099

(22) Filed: Feb. 2, 2012

(65) Prior Publication Data

US 2012/0202230 A1 Aug. 9, 2012

(30) Foreign Application Priority Data

Feb. 3, 2011 (JP) ................................ 2011-021593
Jan. 30, 2012 (JP) ................................ 2012-017340

(51) Int. Cl.
*G01N 33/543* (2006.01)
*G01N 33/78* (2006.01)
*G01N 33/84* (2006.01)

(52) U.S. Cl.
CPC .............. *G01N 33/78* (2013.01); *G01N 33/84* (2013.01)

(58) Field of Classification Search
CPC ....... G01N 33/78; G01N 33/84; G01N 33/543
See application file for complete search history.

(56) References Cited

U.S. PATENT DOCUMENTS

| 4,299,812 A | 11/1981 | Coombes |
| 4,467,030 A | 8/1984 | Kleinhammer et al. |
| 4,843,018 A | 6/1989 | Berger et al. |
| 5,252,459 A | 10/1993 | Tarcha et al. ..................... 435/6 |
| 5,420,016 A * | 5/1995 | Boguslaski et al. ............. 435/12 |
| 2008/0108097 A1 | 5/2008 | Ohmiya et al. .................... 435/8 |
| 2010/0075435 A1* | 3/2010 | Kasagi et al. ................ 436/500 |

FOREIGN PATENT DOCUMENTS

| CN | 101713779 A | 5/2010 | |
| JP | S61-130870 A | 6/1986 | |
| JP | H03-502243 A | 5/1991 | |
| JP | 06-092968 | 4/1994 | ........... C07D 495/04 |
| JP | 6-183952 | 7/1994 | ............... A61K 9/08 |
| JP | H06-183952 A | 7/1994 | |
| JP | 8-43391 | 2/1996 | ........... G01N 33/543 |
| JP | 9-89889 | 4/1997 | ............. G01N 33/53 |
| JP | 2007-126551 | 5/2007 | ............. C09B 67/08 |
| JP | 2010-53118 | 3/2010 | ........... C07D 495/04 |
| SU | 1484094 A1 | 1/1994 | |
| WO | 89/06363 A1 | 7/1989 | |

OTHER PUBLICATIONS

Diamandis et al., Immunoassay, The Avidin-Biotin System, Chapter 11, pp. 237-255, 1996.*
Sonan et al., "Fundamental and clinical evaluation of TSH and thyroid hormone measurement by electrochemiluminescence immunoassay system Modular Analytics (EE)," J. Med. Pharm. Sci., 46(5):759-771 (2001) (partial translation enclosed).
Takagi et al., "Study of trace substances in serum by Elecsys reference value, Part 1 thyroid hormone," Equipment and Reagent, 23(4): 265-271 (2000) (full translation enclosed).
Bapeks product information sheet for "Biotinyl-1-amino-3,6-dioxa-8-octanamine.HCl" and "Boc-1-amino-3,6-dioxa-8-octanamine" obtained from http://www.bapeks.com/page/10&search=dadoo (2008).
Patzl et al., "Determination of Autoantibodies to Thyroglobulin, Thyroxin and Triiodothyronine in Canine Serum," J Vet Med A Physiol Pathol Clin Med., 50:72-78 (2003).
Extended European Search Report issued in corresponding European Patent Application No. 12153732.8 dated Apr. 12, 2012.
Ithakissios et al., "Immune and Non-Immune T4 Radioassays Utilizing Albumin Magnetic Microparticles," Clinica Chimica Acta, 84: 69-84 (1978).
Seth et al., "Solid-Phase Radioimmunoassay of Thyroxine in Untreated Serum," Clinical Chemistry, 21: 1406-1413 (1975).
Office Action issued in corresponding Chinese Patent Application No. 201210028196.6 dated Aug. 12, 2014, English portions only.
Office Action issued in corresponding Japanese Patent Application No. 2012-017340 dated Sep. 18, 2015.
S. Görög ed., Advances in Steroid Analysis '93, Akad. Kiadó. Budapest, pp. 111-117 (1993).
Hermanson, Bioconjugate Techniques, 1996, Elsevier, pp. 372-379.
Kaiser et al., "Biotinylated Steroid Derivatives as Ligands for Biospecific Interaction Analysis with Monoclonal Antibodies Using Immunosensor Devices", Analytical Biochemistry, 282:173-185 (2000).
Kellie et al., "Chemistry of Steroid-Protein Conjugate Formation", Alpha Omega Publishing Ltd., pp. 33-46 (1975).
Matthew et al., "An overview of electrochemiluminescent (ECL) technology in laboratory investigations", Kathmandu University Medical Journal, 3(1), Issue 9:91-93 (2005).
Novakovskii et al., "The Biotin-Thryoxin Conjugate as a Bifunctional Ligand of Binding Proteins", Russian Journal of Bioorganic Chemistry, 35(2):178-191 (2009); English abstract on p. 191.

(Continued)

Primary Examiner — Gary W Counts
(74) Attorney, Agent, or Firm — Morgan, Lewis & Bockius LLP

(57) ABSTRACT

A liquid reagent of a stabilized thyroid hormone-immobilized carrier, by which a thyroid hormone can be measured easily in a short time and at low cost, is provided. The liquid reagent of a thyroid hormone-immobilized carrier according to the present invention includes: a thyroid hormone-immobilized carrier; and a solvent, and a pH of the solvent containing the thyroid hormone-immobilized carrier is in a range from 8.7 to 11.5. The detection of a thyroid hormone using the liquid reagent of the present invention can be carried out by competitively binding a thyroid hormone in a sample and the thyroid hormone-immobilized carrier in the liquid reagent with an anti-thyroid hormone antibody and detecting a composite of the thyroid hormone-immobilized carrier and the anti-thyroid hormone antibody.

8 Claims, No Drawings

(56) References Cited

OTHER PUBLICATIONS

Patzl et al., "Determination of Autoantibodies to Thyroglobulin, Thyroxin and Triiodothyronine in Canine Serum", J. Vet. Med. A. 50:72078 (2003).
Savage et al., Avidin-Biotin Chemistry: A Handbook, Rockford, Illinois: Pierce Chemical Company, pp. 26, 53, 54, 66, 71, 74, 77, 83 and 256, (1992).
Tanaka et al., "Novel and Sensitive Noncompetitive (Two-Site) Enzyme Immunoassay for Haptens With Amino Groups", Journal of Clinical Laboratory Analysis, 4:208-212 (1990).

* cited by examiner

LIQUID REAGENT OF THYROID HORMONE-IMMOBILIZED CARRIER AND USE THEREOF

CROSS-REFERENCE TO RELATED APPLICATIONS

This application claims priority to JP Application No. 2011-021593, filed Feb. 3, 2011 and JP Application No. 2012-017340, filed Jan. 30, 2012, which are hereby incorporated by reference in their entirety.

BACKGROUND OF THE INVENTION

The present invention relates to a liquid reagent of a thyroid hormone-immobilized carrier and use thereof, specifically a method for stabilizing a thyroid hormone-immobilized carrier in a solvent, a method for producing the liquid reagent, and a method and kit for detecting a thyroid hormone.

The thyroid hormones are hormones secreted from the thyroid and have an effect of improving a metabolic rate of cells of a whole body by acting on the cells. As the thyroid hormones, for example, triiodothyronine (T3) and thyroxine (T4) are known. Patients having thyroid dysfunctions such as hyperthyroidism (e.g., Basedow disease) caused by excessively secreting thyroid hormones, hypothyroidism (e.g., Hashimoto disease) caused by lack of secretion of thyroid hormones, and the like have been increased in recent years. Therefore, it is important to accurately measure the thyroid hormones in clinical examinations and the like.

In order to measure the thyroid hormones, for example, competitive immunoassay using an anti-thyroid hormone antibody has been widely employed (see JP H9-89889 A, 2010-53118 A, and Kathmandu University Medical Journal (2005), Vol. 3, No. 1, Issue 9, pp. 91-93). The measurement system of this competitive immunoassay is that thyroid hormones in a sample and those in a reagent are competitively reacted with anti-thyroid hormone antibodies. In the competitive immunoassay, a three-reagent kit is generally used. The kit is composed of a labeled antibody as a first reagent, a biotinylated thyroid hormone as a second reagent, and an avidin-immobilized carrier as a third reagent, and the reagents are stored individually. The measurement using the three-reagent kit is carried out as follows, for example. That is, first, a sample and a labeled antibody are mixed with each other so that a thyroid hormone in the sample and the labeled antibody are bound to each other. Thus, a mixture is obtained. Then, a biotinylated thyroid hormone and an avidin-immobilized carrier are mixed with the mixture. Whereby, a composite of an unreacted labeled antibody that has not been bound to the thyroid hormone in the sample, the biotinylated thyroid hormone, and the avidin-immobilized carrier is formed by an antigen-antibody reaction and an avidin-biotin bond. Thereafter, the composite is separated, and the labeled antibody in the composite is detected. The thyroid hormone in the sample and the biotinylated thyroid hormone are competitively bound to the labeled antibody. Therefore, the labeled antibody binding to the thyroid hormone in the sample can be measured by detecting the labeled antibody in the composite. Whereby, the thyroid hormone in the sample can be measured indirectly. However, in the measurement using the three-reagent kit, it is necessary to mix the three reagents every time the measurement. Therefore, an operation becomes complicated, requires time, and involves a high cost.

BRIEF SUMMARY OF THE INVENTION

For the above-described reason, it is considered using a two-reagent kit containing: a thyroid hormone-immobilized carrier obtained by binding a biotinylated thyroid hormone to an avidin-immobilized carrier; and a labeled antibody. However, the thyroid hormone-immobilized carrier has low stability. Therefore, for example, storing the thyroid hormone-immobilized carrier as a reagent for a long period of time causes a problem in that activity is reduced as compared with the reagent before the storage.

The present invention provides a liquid reagent of a thyroid hormone-immobilized carrier, the liquid reagent containing: a thyroid hormone-immobilized carrier; and a solvent, wherein a pH of the solvent containing the thyroid hormone-immobilized carrier is in a range from 8.7 to 11.5.

The present invention also provides a method for stabilizing a thyroid hormone-immobilized carrier in a solvent, the method including: setting a pH of a solvent containing a thyroid hormone-immobilized carrier in a range from 8.7 to 11.5.

The present invention also provides a method for producing a liquid reagent of a thyroid hormone-immobilized carrier, the method including: a stabilizing step of stabilizing a thyroid hormone-immobilized carrier in a solvent, wherein the stabilizing step is carried out by the stabilization method of the present invention.

The present invention also provides a method for detecting a thyroid hormone, the method including: a binding step of competitively binding a thyroid hormone in a sample and a thyroid hormone-immobilized carrier in the liquid reagent of the present invention to an anti-thyroid hormone antibody; and a detecting step of detecting a composite of the thyroid hormone-immobilized carrier and the anti-thyroid hormone antibody.

The present invention also provides a kit for detecting a thyroid hormone, the kit containing: the liquid reagent of the present invention; and an anti-thyroid hormone antibody, wherein the kit is for use in the detection method of the present invention.

According to the present invention, the thyroid hormone-immobilized carrier can be stabilized by setting the pH of the liquid reagent in the predetermined range. Therefore, for example, the thyroid hormone-immobilized carrier can be stored for a long period of time. Thus, according to the present invention, for example, it is not necessary to prepare a thyroid hormone-immobilized carrier every time a measurement as conventional, so that a thyroid hormone can be measured easily in a short time and at low cost. Therefore the present invention is very useful in clinical examinations and the like.

DETAILED DESCRIPTION OF THE INVENTION

<Liquid Reagent of Thyroid Hormone-Immobilized Carrier>

The liquid reagent of the present invention is, as mentioned above, characterized in that it contains: a thyroid hormone-immobilized carrier; and a solvent, wherein a pH of the solvent containing the thyroid hormone-immobilized carrier is in a range from 8.7 to 11.5.

In the present invention, a pH of the solvent means a pH of the solvent containing all components of the liquid reagent. Hereinafter, the pH of the solvent containing the thyroid hormone-immobilized carrier is referred to as the "pH of the liquid reagent". The lower limit of the pH of the liquid reagent is 8.7 and for example, 8.8 or 9. The upper limit of the pH of the liquid reagent is 11.5, preferably 11, more preferably 10.5, 9.5, 9.4, or 9.2. The range of the pH of the liquid reagent is, as mentioned above, from 8.7 to 11.5, preferably from 8.7 to 11, more preferably from 8.7 to 10.5. The range of the pH is, for example, from 8.7 to 9.5, from 8.7 to 9.4, or from 8.7 to 9.2. The range of the pH is, for example, from 8.8 to 11 or from 9 to 11 and preferably from 8.8 to 10.5, from 9 to 10.5, from 9 to 9.5, from 9 to 9.4, or from 9 to 9.2.

The solvent of the liquid reagent may further contain other component besides the thyroid hormone-immobilized carrier, for example. The other component is not particularly limited, and examples thereof include a surfactant, a dispersant, a preservative, a salt, a metal salt, a protein, a sugar, an amino acid, and a chelating reagent.

The solvent is not particularly limited, and examples thereof include water, a buffer solution, a serum, and a plasma. The solvent preferably is the buffer solution because it allows the pH of the liquid reagent to be easily set in the above-described range, for example. The buffer solution is not particularly limited, and examples thereof include a tris buffer solution, a phosphate buffer solution, an acetate buffer solution, a borate buffer solution, a citrate buffer solution, a veronal buffer solution, and various Good buffer solutions. In the case where the solvent is the buffer solution, the concentration of the buffer solution in the liquid reagent is, for example, from 0.1 to 2000 mmol/l, preferably from 1 to 1000 mmol/l, more preferably from 10 to 500 mmol/l.

Examples of the immobilized thyroid hormone in the thyroid hormone-immobilized carrier include thyroxine (hereinafter, referred to as T4), 3,3',5-L-triiodothyronine (hereinafter, referred to as T3), and derivatives thereof. In the present invention, it is only necessary that the immobilized thyroid hormone competes with the thyroid hormone in the sample and binds to an anti-thyroid hormone antibody. Therefore, the derivative of T4 may be, for example, an epitope recognized by the anti-thyroid hormone antibody or a substance having the epitope, and the derivative of T3 may be, for example, an epitope recognized by the anti-thyroid hormone antibody or a substance having the epitope. Examples of the derivatives include 3-iodo-L-tyrosine, 3-iodo-L-thyronine, 3,5-diiodo-L-tyrosine, 3,5-diiodo-D-tyrosine, 3,5-diiodo-L-thyronine, 3,5-diiodo-D-thyronine, 3,3',5-D-triiodo thyronine, 3,3',5'-L-triiodothyronine (reverse T3), and D-thyroxine. The type of the thyroid hormone to be immobilized is not particularly limited and can be decided as appropriate according to the type of a target thyroid hormone to be detected, for example. The thyroid hormone may be, for example, either one of T3 and T4, a derivative thereof, both of T3 and T4, or a combination of two or more of T3, T4, and the derivatives.

In the thyroid hormone-immobilized carrier, the number of thyroid hormones to be immobilized per a carrier is not particularly limited and may be one molecule. It is, however, preferred that two or more molecules are immobilized per a carrier. The lower limit of the number of molecules to be immobilized per a carrier is, for example, 1, preferably 10, more preferably 100. The upper limit thereof is not particularly limited and is, for example, $1\times10^{20}$, preferably $1\times10^{15}$, and more preferably $1\times10^{10}$.

The carrier is not particularly limited, and a material, a shape, and a size thereof can be set as appropriate. The material of the carrier is, for example, preferably insoluble to a solvent used in detection of the thyroid hormone. Examples of the material include a magnetic material, a silicate inorganic material, an organic material, and a metal material. Examples of the magnetic material include nickel, cobalt, iron, samarium, neodymium, and alloys thereof. Examples of the silicate inorganic material include glass, a silica gel, bentonite, ceramics, and silicon. Examples of the organic material include a plastic, dextran, a filter paper, a sponge, latex, liposome, active carbon, and a carbon fiber. Examples of the metal material include gold, silver, platinum, palladium, nickel, and alloys thereof. Among them, the material preferably is the magnetic material because it can be handled easily using a magnet or the like, for example. Furthermore, the carrier may serve as a label and can be, for example, a fluorescent carrier such as a fluorescent particle. Examples of the shape of the carrier include a particle, a bar, a sheet, and a porous object, and among them, a particle is preferable. The size of the carrier is not particularly limited, and for example, in the case where the carrier is a particle, the average particle size is preferably from 0.001 to 10000 μm, more preferably from 0.01 to 1000 μm, particularly preferably from 0.1 to 100 μm. The carriers may be used alone or in a combination of two or more of them.

The thyroid hormone-immobilized carrier may be, for example, the one obtained by directly or indirectly immobilizing the thyroid hormone on the carrier. The indirect immobilization is not particularly limited and can be, for example, immobilization by binding the thyroid hormone and the carrier to each other via a linker. The linker preferably is a combination of linkers having specific binding properties to each other. In the thyroid hormone-immobilized carrier, it is preferred that, for example, the thyroid hormone and the carrier are bound to each other via a bond between a first linker and a second linker binding to the first linker. Examples of the combination of the first linker and the second linker include a combination of biotin and avidin and a combination of biotin and streptavidin. Any of the first linker and the second linker may be biotin, for example. In the present invention, the biotin may be, other than biotin, a derivative thereof, for example, the avidin may be, other than avidin, a derivative thereof, for example, and the streptavidin may be, other than streptavidin, a derivative thereof. The linker may be, for example, a molecule or a protein. Examples of the protein include albumin and globulin.

In the thyroid hormone-immobilized carrier, for example, it is preferred that the thyroid hormone is immobilized on the carrier via a biotin-avidin bond or a biotin-streptavidin bond. The thyroid hormone-immobilized carrier can be, for example, a composite of a thyroid hormone to which the first linker has been added and a carrier to which the second linker has been added. Specific examples thereof include a composite of a biotinylated thyroid hormone and an avidin-immobilized carrier, a composite of a biotinylated thyroid hormone and a streptavidin-immobilized antibody, a composite of an avidinized thyroid hormone and a biotinylated immobilized carrier, and a composite of a streptavidinized thyroid hormone and a biotin-immobilized carrier.

A method for preparing the thyroid hormone-immobilized carrier is not particularly limited. The thyroid hormone-immobilized carrier can be prepared by causing the thyroid hormone and the carrier to react with each other, for example. Specifically, for example, as mentioned above, the thyroid hormone-immobilized carrier can be prepared by binding the first linker and the second linker to each other through causing a thyroid hormone to which the first linker has been added and a carrier to which the second linker has been added to react with each other. A combination of the thyroid hormone to which the first linker has been added and the carrier to which the second linker has been added is not particularly limited. Examples thereof include a combination of a biotinylated thyroid hormone and an avidin-immobilized carrier, a combination of a biotinylated thyroid hormone and a streptavidin-immobilized carrier, a combination of an avidinized thyroid hormone and a biotinylated immobilized carrier, and a combination of a streptavidinized thyroid hormone and a biotin-immobilized carrier. Commercially available products may be used as the thyroid hormone to which the first linker has been added and the carrier to which the second linker has been added, or they may be prepared by conventionally known methods, for example. Specifically, as the streptavidin-immobilized carrier "Dynabeads (registered trademark) MyOne™Streptavidin T1" (trade name) produced by Dynal biotech can be used, for example. The thyroid hormone or the carrier can be biotinylated using, for example, a commercially available kit, specifically, "Biotin Labeling Kit-NH2" (trade name) produced by DOJINDO LABORATORIES.

The reaction between the thyroid hormone to which the first linker has been added and the carrier to which the second linker has been added can be performed in a solvent, for example. The solvent is not particularly limited, and for example, water, a buffer solution, or the like can be used. The buffer solution is not particularly limited, and examples thereof include a tris buffer solution, a phosphate buffer solution, an acetate buffer solution, a borate buffer solution, a citrate buffer solution, a veronal buffer solution, and various Good buffer solutions. The concentration of the buffer solution in the reaction solution is, for example, from 0.1 to 2000 mmol/l, preferably from 1 to 1000 mmol/l, and more preferably from 10 to 500 mmol/l. The pH of the reaction solution is, for example, from 4 to 11, preferably from 5 to 10, and more preferably from 6 to 9. The solvent may contain the other component besides the thyroid hormone to which the first linker has been added and the carrier to which the second linker has been added. The other component is not particularly limited, and examples thereof include a surfactant, a dispersant, a preservative, a salt, a metal salt, a protein, a sugar, an amino acid, and a chelating reagent.

Conditions of the reaction between the thyroid hormone to which the first linker has been added and the carrier to which the second linker has been added are not particularly limited and can be decided as appropriate according to the combination of the linkers, the type of the carrier, and the like, for example. The temperature of the reaction is, for example, from 0° C. to 50° C. and preferably from 4° C. to 40° C. The time of the reaction is, for example, from 5 to 360 minutes and preferably from 30 to 120 minutes. The ratio between the thyroid hormone to which the first linker has been added and the carrier to which the second linker has been added to be added in the reaction solution is not particularly limited. The molar ratio (A:B) between the first linker (A) and the second linker (B) is preferably from 1:0.01 to 1:100 and more preferably from 1:0.1 to 1:10.

As mentioned above, when the number of thyroid hormones immobilized per a carrier is plural, it is preferred that a plurality of second linkers are added to a carrier, and thyroid hormones are bound to the respective second linkers via the first linkers, for example.

The concentration of the thyroid hormone-immobilized carrier in the liquid reagent is not particularly limited. The concentration is, for example, in the range from 1 to 10000 µg/ml, preferably from 5 to 5000 µg/l, and more preferably from 10 to 1000 µg/ml. The liquid reagent may contain, for example, one type of the thyroid hormone-immobilized carrier or two or more types thereof. In the latter case, the concentrations of the respective thyroid hormone-immobilized carriers are not particularly limited. For example, each of the concentrations of the thyroid hormone-immobilized carriers may be in the above-mentioned range, or the concentration of the total of the thyroid hormone-immobilized carriers may be in the above-mentioned range.

A method for preparing the liquid reagent in not particularly limited, and can be achieved by setting the pH of the solvent containing the thyroid hormone-immobilized carrier in the above-mentioned range, for example. A method for adjusting the pH is not particularly limited. For example, the thyroid hormone-immobilized carrier and the other component as required are added to a solvent (buffer solution) having a pH that has been previously set in the above-mentioned range and having a buffer capacity, and by the buffer capacity of the solvent, the pH of the liquid reagent can be set in the above-mentioned range. On the other hand, the thyroid hormone-immobilized carrier and the other component as required are added to a solvent, the pH of the liquid reagent can be set in the above-mentioned range by adjusting the pH of the solvent using a pH adjusting reagent. Examples of the pH adjusting reagent include acid, alkali, and a buffer agent.

According to the liquid reagent of the present invention, for example, when the liquid reagent is stored at 37° C., an activity of the thyroid hormone-immobilized carrier can be maintained for about 7 days. Specifically, assuming that the activity of the thyroid hormone-immobilized carrier in the liquid reagent immediately after the production thereof is 100%, for example, the activity of the same after storing it at 37° C. for 7 days can be maintained at, for example, 80% or more, preferably 85% or more, and more preferably 90% or more.

The liquid reagent is very useful in measurements and the like of thyroid hormones in clinical examinations such as treatments and diagnoses, for example. The use of the liquid reagent is not limited to the clinical examinations, and for example, it can be applied in detections of thyroid hormones in a wide field such as biochemistry or the like except the diagnoses and the treatments, for example. The same applies hereinafter.

<Method for Stabilizing Thyroid Hormone-Immobilized Carrier>

The stabilization method of the present invention is, as mentioned above, characterized in that it includes: setting a pH of a solvent containing a thyroid hormone-immobilized carrier in a range from 8.7 to 11.5. The stabilization method of the present invention is characterized in that the pH of the solvent containing the thyroid hormone-immobilized carrier is set in the above-mentioned range, and the other steps and conditions are not at all limited. The pH of the solvent can be set with reference to the above-mentioned explanation for the liquid reagent of the present invention, for example.

<Method for Producing Liquid Reagent of Thyroid Hormone-Immobilized Carrier>

The production method of the present invention is, as mentioned above, characterized in that it includes: a stabilizing step of stabilizing a thyroid hormone-immobilized carrier in a solvent, and the stabilizing step is carried out by the stabilization method of the present invention. The production method of the present invention is characterized in that the stabilizing step is carried out by the stabilization method of the present invention, and the other steps and conditions are not at all limited. The production method of the present invention can be explained with reference to the above-mentioned explanations for the liquid reagent of the present invention and for the stabilization method of the present invention.

<Method for Detecting Thyroid Hormone>

The detection method of the present invention is, as mentioned above, characterized in that it includes: a binding step of competitively binding a thyroid hormone in a sample and a thyroid hormone-immobilized carrier in the liquid reagent of the present invention to an anti-thyroid hormone antibody; and a detecting step of detecting a composite of the thyroid hormone-immobilized carrier and the anti-thyroid hormone antibody.

In the present invention, "competitively binding" means not only simultaneously binding a thyroid hormone in a sample and a thyroid hormone-immobilized carrier in the liquid reagent to the anti-thyroid hormone antibody, but also binding either one of the thyroid hormone in the sample and the thyroid hormone-immobilized carrier in the liquid reagent to the anti-thyroid hormone antibody and thereafter binding the other to a free anti-thyroid hormone antibody.

A method for detecting a composite of the thyroid hormone-immobilized carrier and the anti-thyroid hormone antibody in the detecting step is not particularly limited. The detection of the composite may be achieved by detecting a label of a labeled anti-thyroid hormone antibody used as the anti-thyroid hormone antibody in the composite, for example. The detection of the composite may be achieved by detecting a carrier that serves as the above-mentioned label and is used as a carrier of the thyroid hormone-immobilized carrier in the composite, for example. In this case, the anti-thyroid hormone antibody may be a labeled antibody or unlabeled antibody, for example. The carrier serving as a label can be, for example, the above mentioned fluorescent carrier such as a fluorescent particle.

The thyroid hormone to be detected of the present invention can be, for example, any of T4, T3, and derivatives thereof. The derivatives can be, for example, those mentioned above. In the present invention, the thyroid hormone to be detected may be, for example, one type thereof or two or more type thereof. In the present invention, the anti-thyroid hormone antibody and the immobilized thyroid hormone of the thyroid hormone-immobilized carrier can be selected according to the type of the thyroid hormone to be detected, for example.

The sample is not particularly limited and can be, for example, a biological sample or the like. The biological sample can be, for example, blood or the like. Examples of the blood include whole blood, a serum, and plasma. The sample can be used as it is or as a diluent by suspending, dispersing, or dissolving the sample in a solvent, for example. As the solvent, above-mentioned solvent can be used, for example. The sample preferably is a liquid sample because it can be easily handled, for example.

In the anti-thyroid hormone antibody, the antibody is not particularly limited as long as it is an antibody having binding properties to the thyroid hormone. Examples thereof include immunoglobulin molecules such as IgG, IgA, IgM, IgD, IgE, and IgY and antibody fragments thereof (hereinafter, also referred to as antigen binding fragments) such as Fab, Fab', and F(ab')$_2$. The deviation of the antibody is not particularly limited, and examples thereof include animal species such as human; mammals of nonhuman such as mice, rabbits, cattle, swine, horses, sheep, and goats; and birds such as chickens. The antibody may be produced from a serum of an immune animal by a conventionally known method, or a commercially available antibody may be used, for example. The antibody may be, for example, a polyclonal antibody or a monoclonal antibody.

For example, a labeled anti-thyroid hormone antibody can be used as the anti-thyroid hormone antibody as mentioned above. A label that labels the anti-thyroid hormone antibody is not particularly limited as long as it can be detected. The label can be detected by detecting a signal of developed color, emitted light, fluorescent light, or the like, for example. The label may be a label capable of being detected directly or indirectly, for example. Examples of the former include radioactive isotopes and fluorescent dyes. Examples of the latter include enzymes, transition metal complexes, and nucleic acids.

The enzyme can be indirectly detected by causing it to react with a substrate and detecting developed color, emitted light, fluorescent light, or the like of the substrate. The enzyme is not particularly limited, and examples thereof include peroxidase, alkaline phosphatase, and β-D-galactosidase. The substrate is not particularly limited and can be decided as appropriate according to the type of the enzyme, for example. Examples of the substrate include 2,2'-azino-bis(3-ethylbenzthiazoline-6-sulfonic acid) (ABTS), 3,3',5,5'-tetramethylbenzidine (TMB), diaminobenzidine (DAB), 5-bromo-4-chloro-3-indolyl phosphate (BCIP), 4-methyl-umbelliferyl-β-D-galactoside (4MUG), 3-(2'-spiroadamantane)-4-methoxy-4-(3''-β-D-galactopyranosyl)phenyl-1,2-dioxetane (AMGPD), 4-methylumbelliferyl phosphate, o-phenylenediamine, N,N-dimethylaniline, 4-chlorophenol, N-ethyl-N-sulfopropylaniline, N-ethyl-N-(2-hydroxy-3-sulfopropyl)-m-toluidine, p-hydroxyphenyl propionate, and 4-nitro blue tetrazolium chloride (NBT).

The transition metal complex preferably is, for example, the one emits light by an redox reaction through charging it. Examples of the transition metal complex include ruthenium complexes and osmium complexes. The ruthenium complex preferably is a ruthenium pyridine complex such as tris(2,2'-bipyridyl) ruthenium (II) or the like, for example.

Labeling of the anti-thyroid hormone antibody with the label is not particularly limited and can be performed by a conventionally known method. In the case where the label is alkaline phosphatase, a labeled anti-thyroid hormone antibody can be prepared using Alkaline Phosphatase Labeling Kit-SH (trade name) produced by DOJINDO LABORATORIES.

In the present invention, the binding step is, as mentioned above, a binding step of competitively binding a thyroid hormone in a sample and a thyroid hormone-immobilized carrier to an anti-thyroid hormone antibody. The binding step is, for example, a composite forming step, and specifically, it is preferably a composite forming step of forming a first composite of the anti-thyroid hormone antibody and the thyroid hormone in the sample and a second composite of the anti-thyroid hormone antibody and the thyroid hormone-immobilized carrier. The first composite is formed by an antigen-antibody reaction between the anti-thyroid hormone antibody and the thyroid hormone in the sample. The second composite is formed by an antigen-antibody reaction between the anti-thyroid hormone antibody and the thyroid hormone in the thyroid hormone-immobilized carrier.

The composite forming step can be carried out in a reaction solution, for example. The solvent in the reaction solution is not particularly limited, and examples thereof include a tris buffer solution, a phosphate buffer solution, an acetate buffer solution, a borate buffer solution, a citrate buffer solution, a veronal buffer solution, and various Good buffer solutions. The pH of the reaction solution is not particularly limited and is, for example, preferably in the range from 4 to 11, more preferably from 6 to 9, and particularly preferably from 7 to 8.

In the composite forming step, the liquid reagent of the present invention is used as the thyroid hormone-immobilized carrier. The anti-thyroid hormone antibody may be in a dry form or a wet form and is, however, preferably used as a liquid reagent because handling is easy, for example. The liquid reagent of the anti-thyroid hormone antibody is, for example, in a form in which a solvent contains the anti-thyroid hormone antibody. The solvent is not particularly limited, and examples thereof include water and buffer solutions. Examples of the buffer solutions include those mentioned above. The pH of the liquid reagent of the anti-thyroid hormone antibody is not particularly limited and is, for example, preferably in the range from 4 to 11, more preferably from 6 to 9, and particularly preferably from 7 to 8. Regarding the liquid reagent of the anti-thyroid hormone antibody, the solvent may further contain the other component besides the anti-thyroid hormone antibody, for example.

The composite forming step is carried out by bringing the sample into contact with the anti-thyroid hormone antibody and bringing the thyroid hormone-immobilized carrier into contact with the anti-thyroid hormone antibody, for example. The order of bringing them into contact with each other is not particularly limited. Specifically, the composite forming step may be, for example, any of the following steps of:

(A1) forming the first composite and the second composite by simultaneously bringing the sample, the anti-thyroid hormone antibody, and the liquid reagent into contact with one another in a reaction solution;

(A2) forming the first composite by bringing the sample and the anti-thyroid hormone antibody into contact with each other in a reaction solution and further forming the second composite by adding the liquid reagent to the reaction solution; and (A3) forming the second composite by bringing the liquid reagent and the anti-thyroid hormone antibody into contact with each other in a reaction solution and further forming the first composite by adding the sample to the reaction solution.

The step (A1) is carried out as follows, for example. A thyroid hormone in a sample and a thyroid hormone-immobilized carrier in a liquid reagent are simultaneously competitively bound to an anti-thyroid hormone antibody in a reaction solution. Therefore, a first composite of the anti-thyroid hormone antibody and the thyroid hormone in the sample and a second composite of the same and the thyroid hormone-immobilized carrier are formed.

The step (A2) is carried out as follows, for example. First, a first composite is formed by binding a thyroid hormone in a sample and a anti-thyroid hormone antibody to each other in a reaction solution. Then, a second composite is formed by binding a free anti-thyroid hormone antibody that has not been bound to the thyroid hormone in the sample and a thyroid hormone-immobilized carrier in the liquid reagent to each other in the reaction solution.

The step (A3) is carried out as follows, for example. First, a second composite is formed by binding a thyroid hormone-immobilized carrier in a liquid reagent and an anti-thyroid hormone antibody to each other in a reaction solution. Then, a first composite is formed by binding a free anti-thyroid hormone antibody that has not been bound to the thyroid hormone-immobilized carrier and a thyroid hormone in a sample to each other in the reaction solution.

In the present invention, the detecting step is, as mentioned above, a step of detecting a composite of the thyroid hormone-immobilized carrier and the anti-thyroid hormone antibody. In the case where the labeled anti-thyroid hormone antibody is used as the anti-thyroid hormone antibody, and the label is detected, the detecting step can also be referred to as a step of detecting the label of the labeled anti-thyroid hormone antibody in the second composite, for example. Furthermore, in the case where a carrier that servers as a label is used as the thyroid hormone-immobilized carrier, and the carrier is detected as a label, the detecting step can also be referred to as a step of detecting the carrier of the thyroid hormone-immobilized carrier in the second composite, for example.

A method for detecting the label is not particularly limited and can be decided as appropriate according to the type of the label, for example. The label can be detected by detecting a signal of developed color, emitted light, fluorescence, or the like, derived from the label, for example. The signal can be detected by visual check or an optical manner, for example. In the latter case, for example, a reflectance, a transmittance, an absorbance, a fluorescence intensity, or the like may be measured using an optical analysis device. The detection of the label may be, for example, a qualitative detection or a quantitative detection. For example, a composite of the thyroid hormone-immobilized carrier and the anti-thyroid hormone antibody can be detected by detecting the label, and from a result of the detection, the thyroid hormone in the sample can be detected indirectly.

In the composite forming step, for example, the amount of forming the second composite depends on the amount of the thyroid hormone in the sample. That is, for example, the amount of forming the second composite is relatively reduced accompanying the increase in the amount of the thyroid hormone in the sample, and the amount of forming the second composite is relatively increased accompanying the reduction in the amount of the thyroid hormone in the sample. Therefore, for example, the amount of the thyroid hormone in the sample can be determined using a calibration curve showing a correlation between the signal intensity derived from the label, corresponding to the amount of forming the second composite, and the amount of the thyroid hormone. The calibration curve can be produced as follows, for example. A first composite and a second composite are formed using the known amount of thyroid hormone under the same conditions as described above. Then, the signal intensity derived from the label in the second composite are detected. Thus, a calibration curve is produced from the known amount of thyroid hormone and the signal intensity of the label.

The detection method of the present invention preferably further includes: a collecting step of collecting the labeled anti-thyroid hormone antibody being bound to the thyroid hormone-immobilized carrier after the binding step, i.e., after the composite forming step and before the detecting step. The collecting step can also be referred to as a step of collecting a composite of the thyroid hormone-immobilized carrier and the labeled anti-thyroid hormone antibody, i.e., the second composite, for example. By collecting the second composite, the second composite can be separated from the first composite and an unreacted labeled anti-thyroid hormone antibody, for example. Therefore, for example, the detection of a label of the labeled-anti-thyroid hormone antibody of the first composite and a label of the unreacted labeled anti-thyroid hormone antibody are excluded, and the label of the labeled anti-thyroid hormone antibody in the second composite can be detected more accurately.

A method for collecting the second composite is not particularly limited and can be set as appropriate according to the type of the carrier, for example. The second composite can be collected from the reaction solution, for example. Examples of the collection method include a method for capturing the carrier of the thyroid hormone-immobilized carrier in the second composite, a centrifugal treatment, a filtration treatment, a precipitation treatment, a membrane separation treatment, and an adsorption treatment. In the case where the carrier is formed of the magnetic material, the second composite can be collected using a magnetic force of a magnet or the like, for example.

The detection method of the present invention may further include a washing step of washing the second composite after collecting the second composite, for example. By this step, for example, when a fraction containing the second composite contains the first composite and the unreacted labeled anti-thyroid hormone antibody, they can be sufficiently removed.

With respect to the detection method of the present invention, when the above-mentioned carrier that serves as a label is used, and the carrier of the thyroid hormone-immobilized carrier in the second composite is detected as the label, an anti-thyroid hormone antibody that has been immobilized on a basal plate such as a container or a plate may be used as the anti-thyroid hormone antibody. In this case, it is preferred that the detection method of the present invention further includes: the washing step of washing the immobilized anti-thyroid hormone antibody after the binding step, i.e., after the composite forming step and before the detecting step, for example. By the washing step, a component that has not been bound to the immobilized anti-thyroid hormone antibody is removed, for example. Therefore, for example, the detection of the carrier of the thyroid hormone-immobilized carrier, which has not been bound to the immobilized anti-thyroid hormone antibody, can be excluded, and the carrier of the thyroid hormone-immobilized carrier, binding to the immobilized anti-thyroid hormone antibody, can be accurately detected as a label.

The detection method of the present invention is described below with reference to an example using a magnetic particle as a carrier of the thyroid hormone-immobilized carrier and an enzyme as a label of the labeled anti-thyroid hormone antibody. This is, however, merely an example and does not limit the present invention.

First, a liquid sample and a labeled anti-thyroid hormone antibody are mixed. Thus, a reaction solution is obtained. Then, in this reaction solution, a thyroid hormone in the liquid sample and the labeled anti-thyroid hormone antibody are bound to each other. Thus, a first composite is formed.

The pH of the reaction is, for example, from 4 to 11, preferably from 6 to 9, and more preferably from 7 to 8. The temperature of the reaction is, for example, from 4° C. to 60° C., preferably from 20° C. to 50° C., and more preferably from 30° C. to 40° C. The time of the reaction is, for example, from 1 to 30 minutes, preferably from 2 to 20 minutes, and more preferably from 5 to 10 minutes. The amount of the labeled anti-thyroid hormone antibody per 1 ml of the reaction solution is, for example, from 0.05 to 5 µg and preferably from 0.1 to 1 µg.

Then, a liquid reagent of the thyroid hormone-immobilized carrier is added to the reaction solution. As the liquid reagent, the liquid reagent of the present invention, having been stored under the condition of pH from 8.7 to 11.5 is used. Therefore, in the reaction solution, an unreacted labeled anti-thyroid hormone antibody that has not been bound to the thyroid hormone in the sample and the thyroid hormone-immobilized carrier are bound to each other. Thus, a second composite is formed.

The pH of the reaction is, for example, from 4 to 11, preferably from 6 to 9, more preferably from 7 to 8. The temperature of the reaction is, for example, from 4° C. to 60° C., preferably from 20° C. to 50° C., and more preferably from 30° C. to 40° C. The time of the reaction is, for example, from 1 to 30 minutes, preferably from 2 to 20 minutes, and more preferably from 5 to 10 minutes. The amount of the thyroid hormone-immobilized carrier to be added per 1 ml of the reaction solution is, for example, from 0.001 to 5 mg and preferably from 0.01 to 1 mg.

Subsequently, the second composite containing the thyroid hormone-immobilized carrier is collected and held using a magnetic force of the magnet. In this case, it is preferred that the magnet is arranged outside of a container containing the reaction solution, and the second composite is collected via a wall of the container. In the state where the second composite is held as described above, the reaction solution in the container is removed. Therefore, the unreacted labeled anti-thyroid hormone antibody can be removed. This separation method is generally called bound (B)/free (F) separation.

Then, the second composite is added to a new reaction solution through releasing the magnetic force. It is preferred that a substrate against a labeling enzyme of the labeled anti-thyroid hormone antibody is added to the reaction solution before or after adding the second composite, for example. The type of the substrate can be decided as appropriate according to the type of the labeling enzyme, for example. The conditions of the reaction solution can be decided as appropriate according to the types of the labeling enzyme and the substrate, for example.

In the reaction solution, the labeled anti-thyroid hormone antibody of the second composite is subjected to an enzyme reaction using the labeling enzyme, and then intensity of signal generated by the enzyme reaction was measured. Conditions of the reaction are not particularly limited. The pH of the reaction is, for example, from 4 to 12, preferably from 6 to 11, and more preferably from 8 to 10. The temperature of the reaction is, for example, from 4° C. to 60° C., preferably from 20° C. to 50° C., and more preferably from 30° C. to 40° C. The time of the reaction is, for example, from 1 to 30 minutes, preferably from 2 to 20 minutes, and more preferably from 5 to 10 minutes.

Then, the amount of the thyroid hormone in the sample is determined using a calibration curve showing a correlation between the amount of the thyroid hormone and the signal intensity.

In the case where the transition metal complex is used as a label of the labeled anti-thyroid hormone antibody, a thyroid hormone can be detected as follows, for example. The detection of the thyroid hormone is the same as mentioned above unless otherwise shown.

The transition metal complex electrochemically emits light by donating electrical energy, for example. Therefore, for example, the transition metal complex is caused to emit light by donating electrical energy to the second composite separated as mentioned above, and the transition metal complex as the label is detected through detection of a signal of this emitted light, and based on the result of this detection, thyroid hormone in the sample can be detected.

When the transition metal complex is used, it is preferred that the electrical energy is donated to the second composite on an electrode in order to donate the electrical energy as mentioned above. The electrode is, for example, a working electrode.

Preferred examples of the transition metal complex include ruthenium complexes, and among them, any of the above-mentioned ruthenium complexes is preferable. When the transition metal complex is used as the label, it is preferable to use tripropylamine (TPA) in combination. By the combined use with TPA, the second composite can emit light as follows. First, by providing a positive potential to the electrode, a divalent ruthenium complex in the second composite is oxidized to a trivalent ruthenium complex, and at the same time, the TPA is oxidized. The oxidized TPA is converted into a TPA radical by dehydrogenation, so that the trivalent ruthenium complex is reduced and changed into a divalent ruthenium complex in the excited state. Then, when the unstable divalent ruthenium complex in the excited state is transited to the stable divalent ruthenium complex, light is emitted. The above-described excitation and light emission were repeated by again providing a positive potential to the divalent ruthenium complex that has been turned into the stable state.

<Kit for Detecting Thyroid Hormone>

The detection kit of the present invention is characterized in that it contains: the liquid reagent of the present invention and an anti-thyroid hormone antibody, and the kit is for use in the detection method of the present invention. The detection kit of the present invention can be explained with reference to the above-mentioned explanations for the liquid reagent of the present invention and for the detection method of the present invention, for example. The detection kit includes the thyroid hormone-immobilized carrier as a reagent, so that the number of reagents used in the detection kit is less as compared with the case of using the three-reagent kit, for example. Thus, the detection kit of the present invention is at low cost.

In the detection kit of the present invention, the anti-thyroid hormone antibody may be in a dry form or a wet form as mentioned above, for example, and is, however, preferably a liquid reagent such as mentioned above because handling is easy, for example. In the detection kit of the present invention, it is preferred that the anti-thyroid hormone antibody and the thyroid hormone-immobilized carrier are stored in the respective containers. The kit may further contain instructions thereof, for example.

EXAMPLES

Next, the example of the present invention is described. The present invention, however, is not limited by the following example.

Example 1

In the present example, a liquid reagent of a thyroid hormone-immobilized carrier was prepared, and storage stability thereof was evaluated.

(1) Preparation of Liquid Reagent of Thyroid Hormone-Immobilized Carrier

L-thyroxine (produced by NACALAI TESQUE, INC.) was biotinylated, and thus obtaining biotinylated T4. The biotinylation was carried out using Biotin Labeling Kit-NH2 (trade name, produced by DOJINDO LABORATORIES) according to the instructions thereof. Then, the biotinylated T4 and a streptavidin-coated magnetic fine particle (trade name: Dynabeads (registered trademark) MyOne™Streptavidin T1, produced by Dynal Biotech) were mixed with each other so that biotin of the biotinylated T4 is bound to streptavidin of the streptavidin-coated magnetic fine particle. Thus, T4-immobilized magnetic particle to which T4 had been immobilized was obtained. The binding between the biotin and the streptavidin was performed in a tris buffer solution as a solvent under the conditions at pH 7.4, 37° C. for 60 minutes. The ratio between the biotinylated T4 and the streptavidin-coated magnetic fine particle to be added in the solvent was set so that the amount of the biotinylated T4 became in excess of the total amount of the streptavidin.

The T4-immobilized magnetic particle was mixed with the following buffer solution 1 so as to have 50 µg/ml, and thus preparing liquid reagents each having a different pH. The respective pHs of the liquid reagents were 8.7, 8.8, 9.0, 9.2, 9.4, 9.5, and 10.5. The T4-immobilized magnetic particle was mixed with the following buffer solution 2 so as to have 50 µg/ml, and thus preparing liquid reagents each having a different pH. The respective pHs of the liquid reagents were 7.0, 7.4, 7.6, 7.8, 8.0, 8.2, 8.4, and 8.6. The liquid reagents each having the pH in the range from 8.7 to 10.5 were used as liquid reagents of Example 1. The liquid reagents each having the pH in the range from 7.0 to 8.6 were used as liquid reagents of Comparative Example 1.

(Buffer Solution 1: pH 8.7-10.5)

| 50 mmol/l | Tris |
| 150 mmol/l | NaCl |
| 0.1% | BSA |
| 0.05% | NaN$_3$ |

(Buffer Solution 2: pH 7.0-8.6)

| 50 mmol/l | Tris |
| 150 mmol/l | NaCl |
| 0.1% | BSA |
| 0.05% | NaN$_3$ |

(2) Measurement of Thyroid Hormone by Competitive Enzyme Immunoassay

An anti-T4 mouse monoclonal antibody was labeled with an enzyme, and thus obtaining an enzyme-labeled antibody. The labeling with the enzyme was carried out using Alkaline Phosphatase Labeling Kit-SH (trade name, produced by DOJINDO LABORATORIES) according to the instructions thereof. Then, the enzyme-labeled antibody was mixed with the following buffer solution 3 so as to have 0.2 µg/ml, and thus preparing an enzyme-labeled antibody solution.

(Buffer Solution 3: pH 7.0)

| 50 mmol/l | Tris |
| 150 mmol/l | NaCl |
| 0.1% | BSA |
| 0.05% | NaN$_3$ |
| 0.025 mmol/l | ZnCl$_2$ |
| 5 mmol/l | MgCl$_2$ |

As a sample, a human serum (n=2) having a known concentration of free T4 was used. 100 µl of the enzyme-labeled antibody solution and 10 µl of the sample were mixed with each other in a tube with a capacity of 1.5 ml (product code: MCT-150-L-C, produced by Axygen), which was then incubated at 37° C. for 5 minutes. After the incubation, a mixed liquid thus obtained and 100 µl of each of the liquid reagents of Example 1 and Comparative Example 1 were mixed with each other, which was then incubated at 37° C. for 5 minutes. Then, a magnet was arranged on an external wall of the tube, and by a magnetic force, the T4-immobilized magnetic particle in the mixed liquid was captured on the interior wall side of the tube. In this state, a liquid in the tube was removed. Subsequently, the magnetic force was released, and a washing solution was added into the tube and was mixed with the T4-immobilized magnetic particle. This washing step was conducted a total of three times. As the washing solution, a tris buffer solution containing 0.05% of Tween20 (registered trademark) was used. The T4-immobilized magnetic particle was again captured, and a liquid in the tube was removed. Then, 500 μl of a liquid containing 0.6 mmol/l 4-methylumbelliferyl phosphate was added thereto and was mixed with the T4-immobilized magnetic particle, which was then incubated at 37° C. for 10 minutes. After the incubation, the T4-immobilized magnetic particle was captured in the same manner as mentioned above, and the liquid in the tube was collected. 50 μl of 2 mol/l NaOH was added to the liquid, a fluorescence intensity of generated 4-methyl umbelliferyl was measured (at a wavelength of 450 nm). The measurement was conducted a total of two times, and the average value of values obtained by the measurements was calculated as a measurement value.

(3) Storage Stability Evaluation

The liquid reagents of Example 1 and Comparative Example 1 were stored at 37° C. for 7 days. The liquid reagents before the storage (0 day) and the liquid reagents after 7 days since the storage started were subjected to competitive enzyme immunoassay shown in the item (2). Then, the amounts of free T4 in samples were measured.

The values ($X_0$) obtained by the measurements using the liquid reagents before the storage and the values ($X_7$) obtained by the measurements using the liquid reagents after 7 days since the storage started were substituted into the following formula (I), so that residual ratios (%) of activity of the T4-immobilized magnetic particle were determined.

Residual ratio (%) of activity=$(X_7/X_0) \times 100$       (I)

A relationship between the pHs of the liquid reagents and the residual ratios of the activity is shown in Table 1 below. As shown in Table 1, residual ratios of the activity with respect to the liquid reagents of Example 1 after the storage, each having a pH of 8.7 or more were higher as compared with the liquid reagents of Comparative Example 1 after the storage, each having a pH of less than 8.7. From these results, it was found that stability of the T4-immobilized magnetic particle is improved by setting the pH of the liquid reagent to 8.7 or more.

TABLE 1

|  | pH of liquid reagent | Residual activity (%) |
|---|---|---|
| Example 1 | 10.5 | 97.8 |
|  | 9.5 | 97.5 |
|  | 9.4 | 96.7 |
|  | 9.2 | 96.0 |
|  | 9.0 | 94.0 |
|  | 8.8 | 96.8 |
|  | 8.7 | 95.7 |
| Comparative Example 1 | 8.6 | 89.8 |
|  | 8.4 | 90.6 |
|  | 8.2 | 89.1 |
|  | 8.0 | 89.3 |
|  | 7.8 | 89.5 |
|  | 7.6 | 88.9 |
|  | 7.4 | 85.2 |
|  | 7.0 | 86.6 |

As described above, according to the present invention, the thyroid hormone-immobilized carrier can be stabilized by setting the pH of the liquid reagent in a predetermined range, so that, for example, the thyroid hormone-immobilized carrier can be stored for a long period of time. Thus, according to the present invention, for example, it is not necessary to prepare the thyroid hormone-immobilized carrier every time a measurement, so that a thyroid hormone can be measured easily in a short time and at low cost. Therefore the present invention is very useful in clinical examinations. The present invention is not limited to be applied to only clinical examinations and can be applied to, for example, detection of thyroid hormone in a wide field such as biochemistry and the like.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A reagent consisting of:
   a stabilized thyroxine-immobilized carrier or a stabilized 3,3',5-L-triiodothyronine-immobilized carrier present in a buffer solution,
   wherein the buffer solution is at a pH in a range of 8.7 to 11.5 and at a concentration of 10 to 500 mmol/l and contains at least one of a surfactant, a dispersant, a preservative, a salt, a protein, a sugar, an amino acid and a chelating reagent,
   wherein the immobilized thyroxine or 3,3',5L-triiodothyronine hormone consists of a thyroxine or 3,3',5L-triiodothyronine hormone directly bound to biotin and the biotin bound directly to the carrier via avidin or streptavidin,
   wherein the reagent is a liquid, the carrier is a magnetic particle containing nickel, cobalt, iron, samarium, neodymium, or alloys thereof and having a particle size of 0.01 to 1,000 μm, and
   wherein the thyroxine-immobilized carrier and the 3,3',5-L-triiodothyronine-immobilized carrier are stabilized by the buffer solution to increase storage time.

2. A kit for detecting thyroxine or 3,3',5-L-triiodothyronine, the kit comprising:
   the liquid reagent according to claim 1; and
   an anti-thyroxine or anti-3,3',5-L-triiodothyronine antibody.

3. The reagent according to claim 1, wherein the buffer solution is at a pH in a range of from 8.7 to 10.5.

4. The reagent according to claim 1, wherein the buffer solution is at a pH in a range of from 8.7 to 9.2.

5. The reagent according to claim 1, wherein the buffer solution is selected from the group consisting of a tris buffer solution, a phosphate buffer solution, an acetate buffer solution, a borate buffer solution, a citrate buffer solution, and a veronal buffer solution.

6. The reagent according to claim 1, wherein the magnetic particle has a particle size of 0.1 to 100 μm.

7. The reagent according to claim 1, wherein the thyroxine-immobilized carrier or the 3,3',5-L-triiodothyronine-immobilized carrier is present in the liquid reagent at a concentration of 1 to 10,000 μg/ml.

8. The reagent according to claim 1, wherein the thyroxine-immobilized carrier or the 3,3',5-L-triiodothyronine-immobilized carrier is present in the liquid reagent at a concentration of 10 to 1,000 μg/ml.

* * * * *